(12) United States Patent
Recanati et al.

(10) Patent No.: US 10,842,371 B2
(45) Date of Patent: Nov. 24, 2020

(54) VAGINAL SPECULUM AND SIDE WALL RETRACTOR

(71) Applicants: Maurice Andre Recanati, New York, NY (US); Katherine Kramer, Philadelphia, PA (US); Mohammad Ali Ozbeki, Novi, MI (US); Jacob Carney, Berkley, MI (US); Avik Chakravarty, Detroit, MI (US); Amanda Nowicki, Plymouth, MI (US); Alexander Von Mach, Birmingham, MI (US); Steven Dudick, Tucson, AZ (US); Maik Huettemann, Grosse Pointe, MI (US); Jay Berman, West Bloomfield, MI (US); Robert Alan Welch, West Bloomfield, MI (US); Rita Semrick, Fresno, CA (US)

(72) Inventors: Maurice Andre Recanati, New York, NY (US); Katherine Kramer, Philadelphia, PA (US); Mohammad Ali Ozbeki, Novi, MI (US); Jacob Carney, Berkley, MI (US); Avik Chakravarty, Detroit, MI (US); Amanda Nowicki, Plymouth, MI (US); Alexander Von Mach, Birmingham, MI (US); Steven Dudick, Tucson, AZ (US); Maik Huettemann, Grosse Pointe, MI (US); Jay Berman, West Bloomfield, MI (US); Robert Alan Welch, West Bloomfield, MI (US); Rita Semrick, Fresno, CA (US)

( * ) Notice: Subject to any disclaimer, the term of this patent is extended or adjusted under 35 U.S.C. 154(b) by 0 days.

(21) Appl. No.: 16/257,345

(22) Filed: Jan. 25, 2019

(65) Prior Publication Data
US 2019/0223708 A1    Jul. 25, 2019

Related U.S. Application Data

(60) Provisional application No. 62/621,674, filed on Jan. 25, 2018.

(51) Int. Cl.
*A61B 1/303*    (2006.01)
*A61B 1/32*    (2006.01)
(Continued)

(52) U.S. Cl.
CPC ............... *A61B 1/303* (2013.01); *A61B 1/32* (2013.01); *A61B 17/42* (2013.01); *A61B 1/07* (2013.01); *A61B 17/02* (2013.01); *A61B 90/30* (2016.02)

(58) Field of Classification Search
CPC .. A61B 1/303; A61B 1/32; A61B 1/07; A61B 17/42; A61B 17/02; A61B 90/30
(Continued)

(56) References Cited

U.S. PATENT DOCUMENTS 3,565,061 A * 2/1971 Reynolds ............... A61B 1/32
                                                                600/220
4,884,559 A * 12/1989 Collins .................... A61B 1/32
                                                                600/205
(Continued)

*Primary Examiner* — Eduardo C Robert
*Assistant Examiner* — David C Comstock
(74) *Attorney, Agent, or Firm* — Jacob M. Ward; Ward Law Office LLC

(57) ABSTRACT

A vaginal speculum and side wall retractor allows clinicians to visualize the cervix and upper vagina by retracting vaginal walls simultaneously. This device is comprised of a handle, a mobile introducer allowing the device to comfortably be inserted vaginally, and a lower blade capable of stabilizing the cervix and a body containing the side wall retractor. This retractor is comprised of a rolled-up sheet of transparent plastic which can be opened through a rotating shaft countersunk in the body of the base. A friction or sprocket gear allows the rotating shaft to open and close the
(Continued)

plastic side wall retractor as well as completely unwinding the transparent plastic sheet so that the device can be removed while leaving surgical instruments in the vagina. The rotating shaft serves as a light guide and brings light from the knob, which contains an LED, into the rolled-up sheet during examinations.

19 Claims, 12 Drawing Sheets

(51) Int. Cl.
A61B 17/42 (2006.01)
A61B 90/30 (2016.01)
A61B 17/02 (2006.01)
A61B 1/07 (2006.01)

(58) Field of Classification Search
USPC ........ 600/206, 208, 210, 213, 215, 220–223
See application file for complete search history.

(56) References Cited

U.S. PATENT DOCUMENTS

| | | | | |
|---|---|---|---|---|
| 4,994,070 | A * | 2/1991 | Waters | A61B 1/32 606/191 |
| 5,318,010 | A * | 6/1994 | Lundberg | A61B 1/32 600/222 |
| 6,364,832 | B1 * | 4/2002 | Propp | A61B 1/303 600/201 |
| 6,432,048 | B1 | 8/2002 | Francois | |
| 8,376,942 | B2 * | 2/2013 | Krauter | A61B 1/303 600/220 |
| 8,460,187 | B2 | 6/2013 | Bouquet | |
| 8,721,538 | B2 * | 5/2014 | Bucholz | A61B 17/0293 600/206 |
| 8,858,431 | B2 * | 10/2014 | Smith | A61B 1/32 600/220 |
| 9,861,349 | B2 * | 1/2018 | Nadershahi | A61B 1/00082 |
| 2003/0069476 | A1 | 4/2003 | Deslauriers et al. | |
| 2008/0058605 | A1 | 3/2008 | Sorensen | |
| 2010/0280627 | A1 * | 11/2010 | Hanes, II | A61B 17/0218 623/23.72 |
| 2012/0078060 | A1 * | 3/2012 | Swift | A61B 1/303 600/220 |

* cited by examiner

VAGINAL SPECULUM AND SIDE WALL RETRACTOR

CROSS-REFERENCE TO RELATED APPLICATIONS

This application claims the benefit of U.S. Provisional Application Ser. No. 62/621,674, filed on Jan. 25, 2018. The entire disclosure of the above application is hereby incorporated herein by reference.

FIELD

The present disclosure relates to handheld medical devices and, more particularly, to handheld medical devices that permit the examination of the vagina and the cervix.

BACKGROUND

Gynecology is an important medical specialty in the field of women's health, concentrating on the health and disease of the female reproductive tract. The lower part of this tract consists of the vulva, the vagina and the cervix. The vaginal speculum is a medical device that allows a clinician to visualize the vaginal canal, which typically is a collapsed space, as well as the cervix, situated at the distal end of the vagina. Typically, the standard vaginal speculum is comprised of two articulating blades, which rotate and/or translate so as to expand the vaginal canal in an anterior-posterior orientation.

While this conventional design has served gynecologists well, the device has multiple limitations. In the United States, the growing number of morbidly obese women, and also the considerable number of women who have had multiple childbirth, pose a unique challenge to the examining clinician. The vaginal walls are no longer supported in such cases and tend to collapse inward. Standard vaginal speculums, which separate the anterior and posterior vaginal walls offer no side wall retraction (and fail to protect the side walls). Thus, examining the cervix in certain patients becomes impossible.

In this domain, the devices of the prior art have drawbacks or are not readily accepted by obstetricians for practical and safety issues. The simplest methods involve adapting traditional speculums with elasticized cylinders (such as by cutting a latex glove to fit over and between the blades). This first approach, such as disclosed in U.S. Pat. No. 6,432,048 to Francois, makes opening the speculum difficult and there is a risk of losing the membrane in the vagina.

A second approach, such as disclosed in U.S. Pat. No. 8,460,187 to Bouquet, involves using multiple moving blades to visualize the cervix. This approach may pinch the patient. Gaps between the blades may also still allow for vaginal folds to obstruct view.

A third approach, such as suggested by U.S. Patent Application Publication No. 2003/0069476 to Deslauriers et al., involves using inflatable mechanisms to retract the vaginal walls. Practically, the inflated member tends to expand also within the lumen of the device, and the mechanism requires a somewhat thick-walled air chamber and sharp instruments (such as a curette). This may damage the airbag and cause a failure of the device.

A fourth approach, such as disclosed in U.S. Patent Application Publication No. 2008/0058605 to Sorensen, involves a ratcheted sheet and mirror concept. This device offers no protection while inserting the device, which could result in vaginal lacerations. The tip design also does not permit for cervical support and stabilization. Due to the rigidity of the device, Sorenson further discloses a mirror, and this arrangement may severely limit a practitioner's ability to cannulate the cervical canal.

There is a continuing need for a device that allows clinicians to have an unobstructed view of the cervix and vaginal walls. Desirably, the device militates against the vaginal side walls collapsing into the field of views.

SUMMARY

In concordance with the instant disclosure, a device that allows clinicians to have an unobstructed view of the cervix and vaginal walls and militates against the vaginal side walls collapsing into the field of views, is surprisingly discovered.

In one embodiment, a vaginal speculum has a main body, an upper blade, and a side wall retractor. The main body includes a handle coupled to a lower blade. The upper blade is removably coupled to the lower blade. The upper blade is configured for one of horizontal displacement and vertical displacement relative to the lower blade. The side wall retractor is disposed on the lower blade. The side wall retractor has a shaft and a rolled sheet. The shaft is configured to unroll the rolled sheet upon rotation of the shaft.

In another embodiment, the upper blade is configured for horizontal displacement relative to the lower blade, and the side wall retractor has a knob. The shaft is configured to unroll the rolled sheet upon rotation of the shaft by the knob. The upper blade is slidably received by the lower blade. The upper blade has a pair of tracks and the lower blade has a pair of corresponding channels for slidably receiving the pair of tracks. The upper blade has a free end with a grip tab that permits for a user to manually pull the upper blade for the horizontal displacement. The grip tab is a semi-circular bridge attached to the free end of the upper blade.

In a further embodiment, the upper blade is configured for vertical displacement relative to the lower blade, and the vaginal speculum has an opening mechanism. The opening mechanism is disposed in the handle configured to cause the vertical displacement of the upper blade. The opening mechanism includes a pair of supports, a grip tab, and a fastener. The pair of supports connect the upper blade and the grip tab. The handle has a pair of channels formed therein. The grip tab is slidably connected to the handle via the channels. The grip tab has an aperture formed therethrough. The handle has a central elongate slot disposed between the pair of channels. The fastener is disposed through the aperture of the grip tab and the central elongate slot of the handle, and is configured to selectively affix the grip tab at a user-defined position along the handle. The upper blade is thereby supported in its vertical displacement by the fastening of the grip tab at the user-defined position.

In an exemplary embodiment, a combined vaginal speculum and side wall retractor is configured to be inserted comfortably and atraumatically. The speculum is capable of retracting the anterior and posterior walls as well as the lateral side walls of the vagina. Further, the speculum is capable of exposing the cervix and vaginal walls in healthy adult women, pediatric-aged patients needing pelvic examination, women with poor vaginal tone, multiparous women, and morbidly obese women.

The speculum has a light source capable of illuminating the entire vaginal cavity and can be removed easily and comfortably. The speculum can be removed while leaving instruments, inserted through it, and which remain within the vaginal cavity after the speculum is removed.

The speculum facilitates the performance of pelvic examinations, collection of Papanicolaou specimens, collection of sexually transmitted infections swabs, gaining trans cervical access to the uterine cavity, performance of endometrial biopsies, performance of colposcopic examination, insertion of surgical instruments such as tenaculum, cervical dilators, curettes, uterine manipulators and hysteroscopes.

The speculum may be removed while instruments (such as a tenaculum or a hysteroscope) inserted through it remain in the vagina. The speculum can be opened to any size the clinician needs. The allows, through transparency and direct exposure, all surfaces of the vagina to be visualized. The speculum allows the cervix to be cupped and manipulated. The speculum is inexpensive to manufacture, made of biosafe materials suitable for placement within a human body, safe to use and has no sharp angles. The speculum may also be sterilized prior to use, and has no small loose parts.

DRAWINGS

The drawings described herein are for illustration purposes only and are not intended to limit the scope of the present disclosure in any way. The above, as well as other advantages of the present disclosure, will become readily apparent to those skilled in the art from the following detailed description, particularly when considered in the light of the drawings described hereafter.

Figure 1:
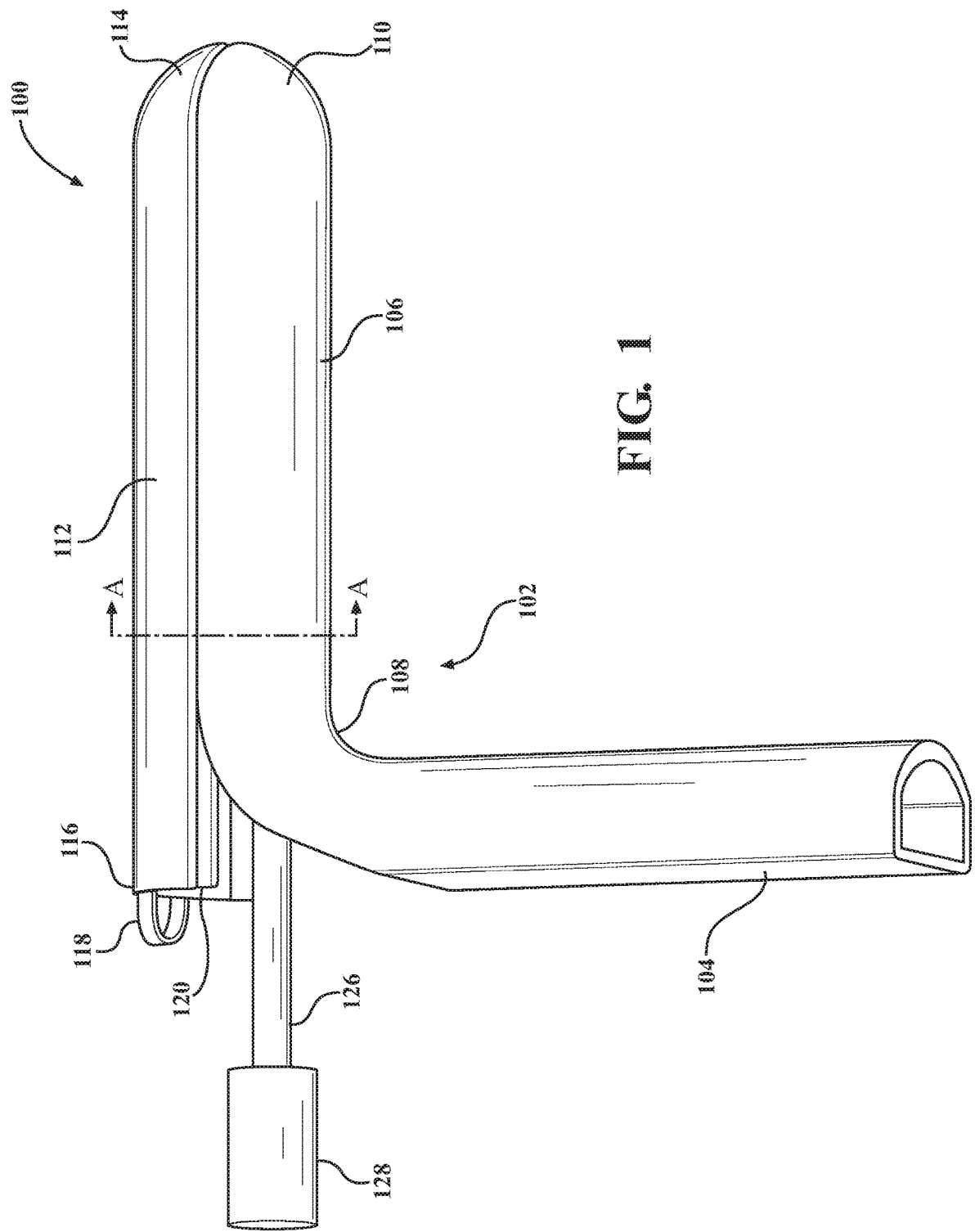
FIG. 1 is a bottom perspective view of a vaginal speculum and side wall retractor according to one embodiment of the present disclosure.
Figure 6:
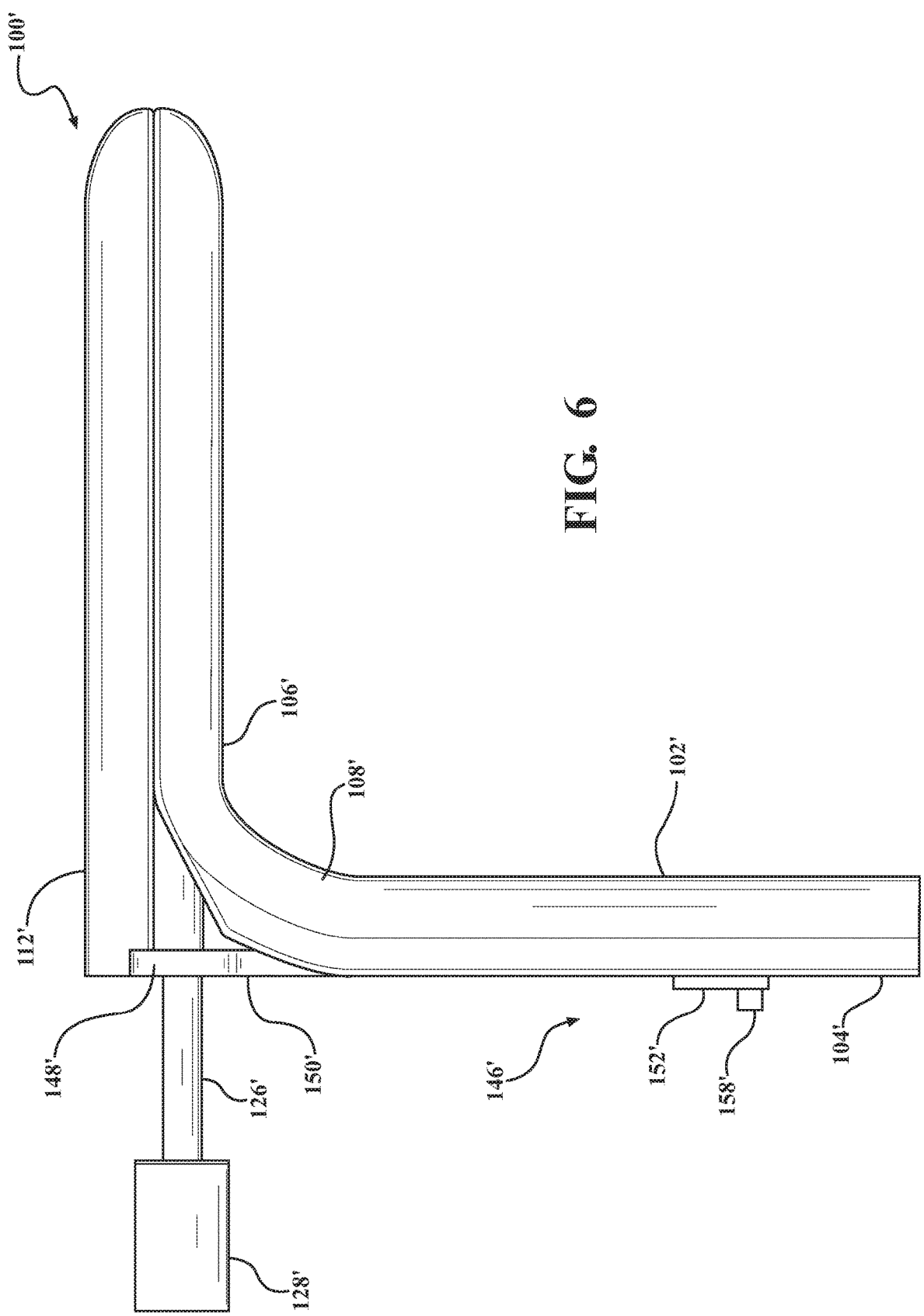
FIG. 6 is a side elevational view of a vaginal speculum and side wall retractor according to another embodiment of this disclosure, with the vaginal speculum and side wall retractor shown in a closed position.
Figure 7:
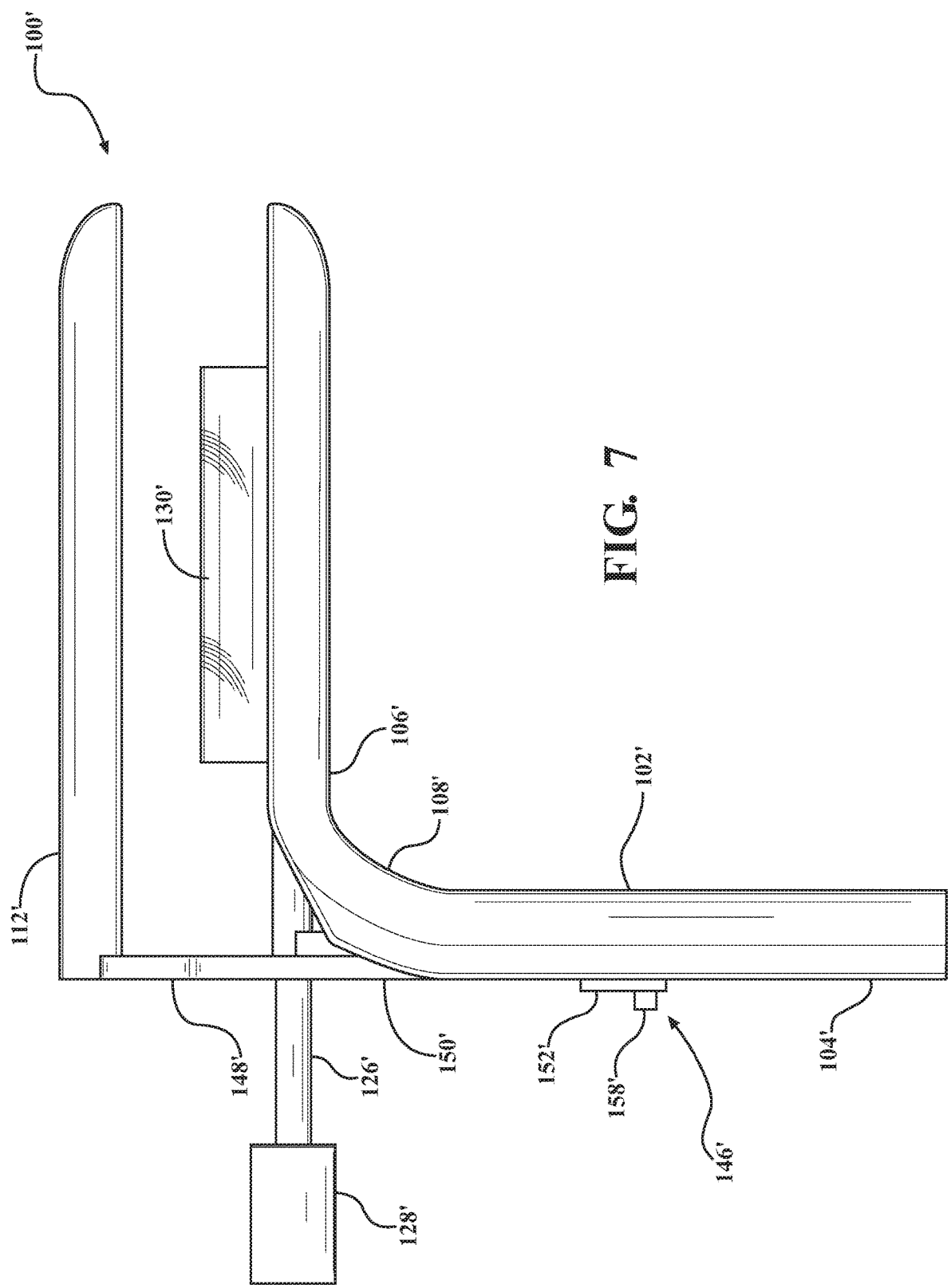
FIG. 7 is a side elevational view of the vaginal speculum and side wall retractor of FIG. 6, shown in an open position.
Figure 10:
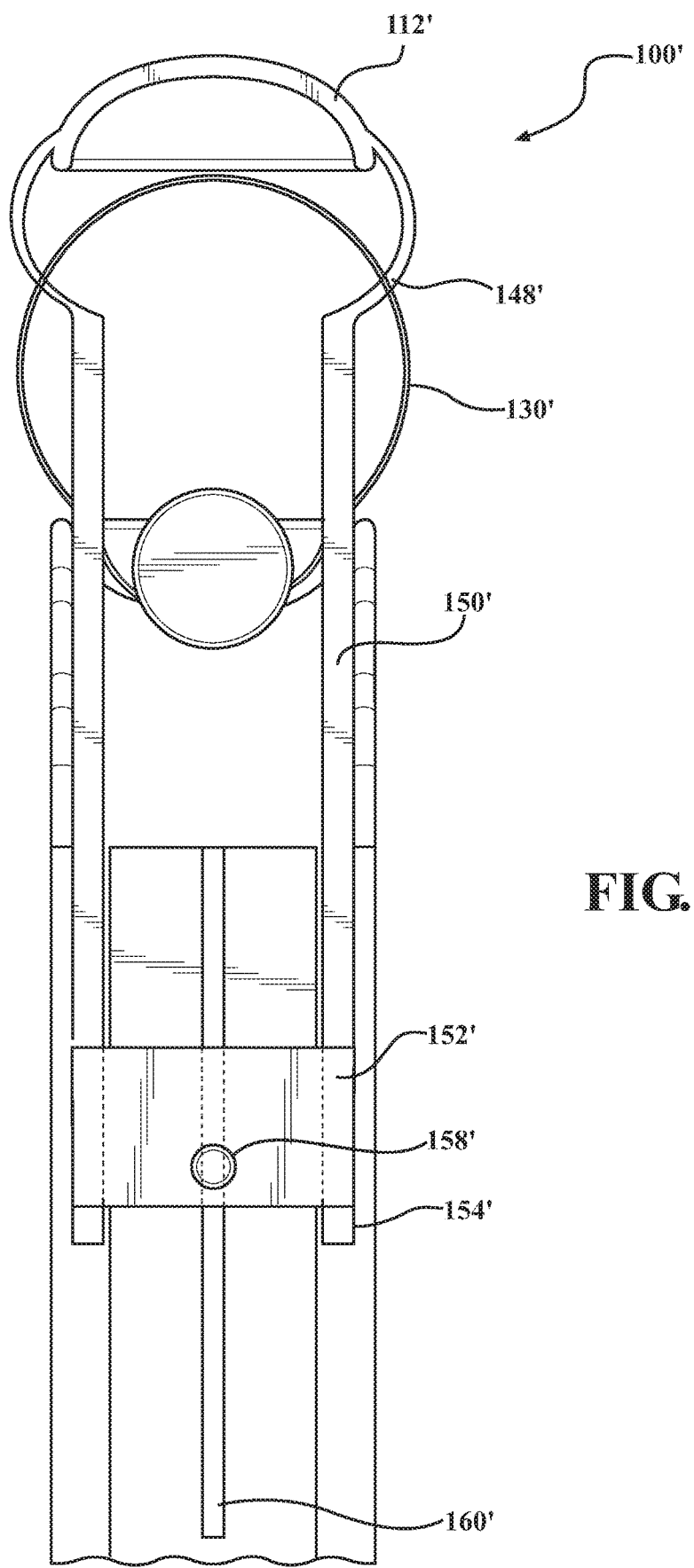
Figure 11:
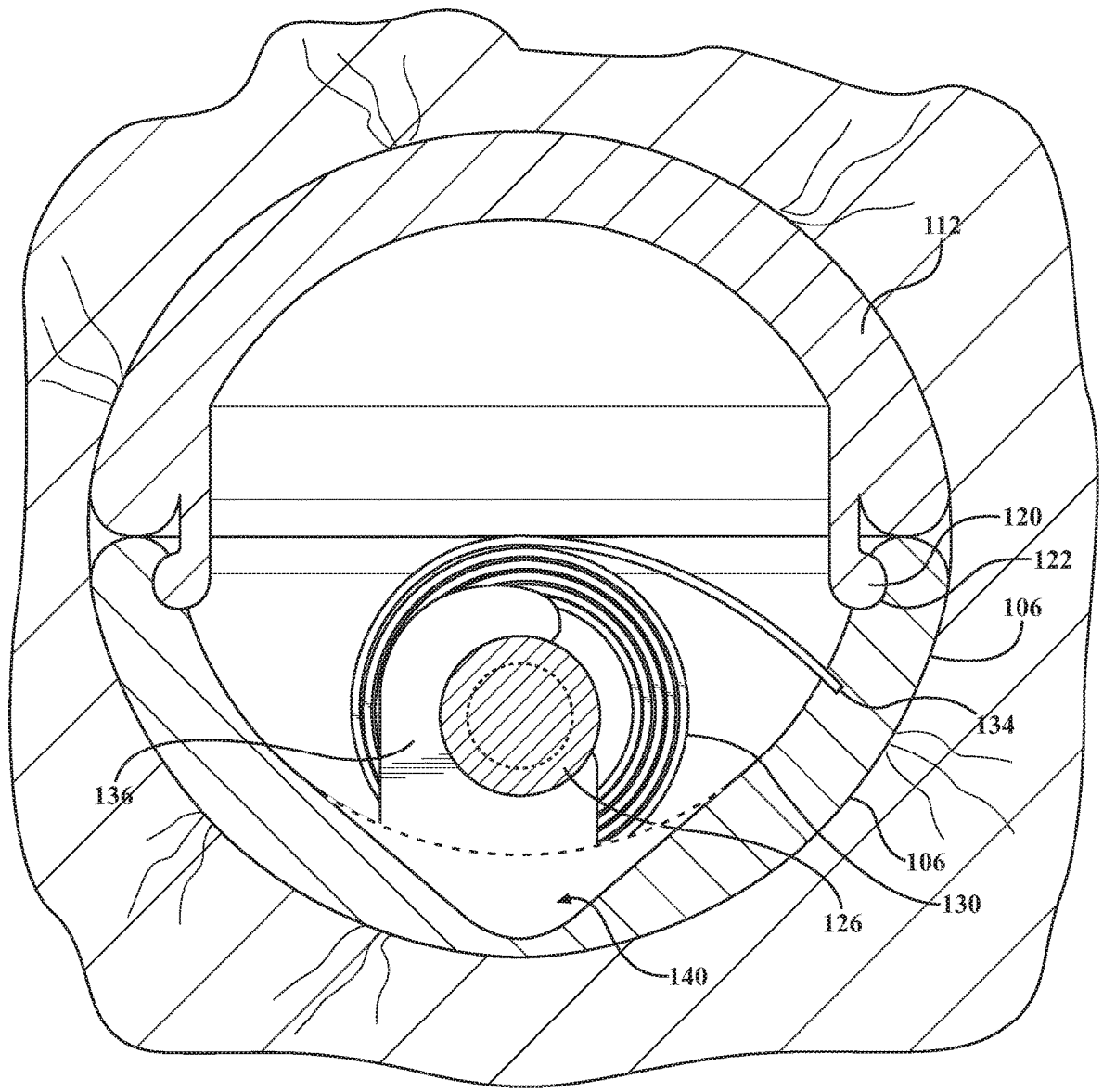
Figure 12:
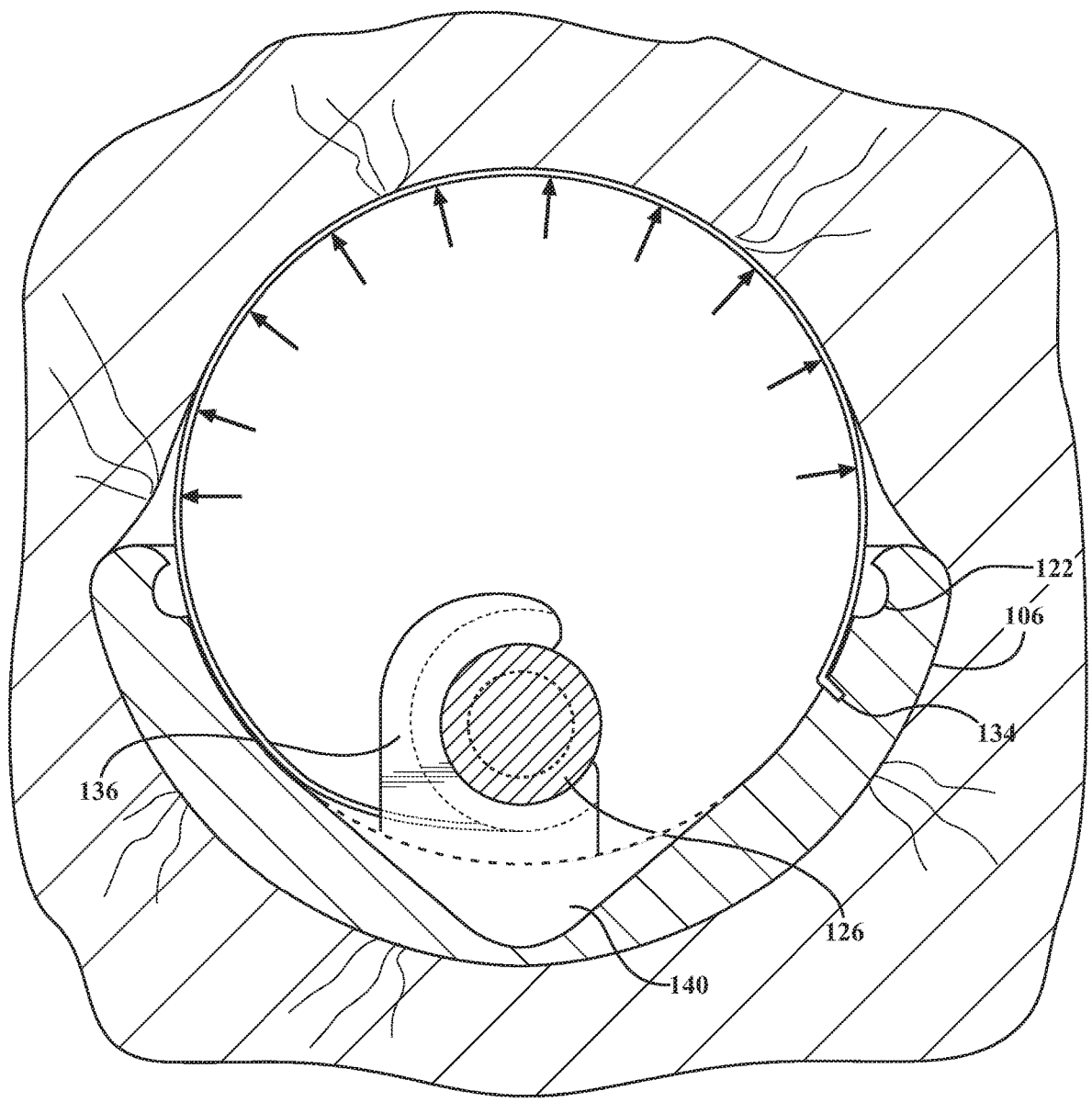

FIG. 10 is a rear elevational view of the vaginal speculum and side wall retractor of FIG. 6, shown in a fully open position FIG. 11 is a cross-sectional rear elevational view of the vaginal speculum and side wall retractor taken through line A-A in FIG. 1, and further shown disposed in a vaginal cavity in a closed position; and FIG. 12 is a cross-sectional rear elevational view of the vaginal speculum shown in FIG. 11, and further shown disposed in the vaginal cavity in an open position with arrows indicating a supporting pressure applied by a rolled sheet of the vaginal speculum and side wall retractor to vaginal side walls.

DETAILED DESCRIPTION

The following description is merely exemplary in nature and is not intended to limit the present disclosure, application, or uses. In respect of the methods disclosed, the order of the steps presented is exemplary in nature, and thus, is not necessary or critical unless otherwise disclosed.

As illustrated in FIGS. 1-12, a vaginal speculum 100 has a main body 102. The main body 102 may be formed of a transparent thermoplastic material such as medical grade polypropylene copolymer by an injection molding process, as a non-limiting example. In another embodiment, the main body 102 may be manufactured from stainless steel. One of ordinary skill in the art may also select other materials and manufacturing methods for the main body 102, as desired.

Figure 2:
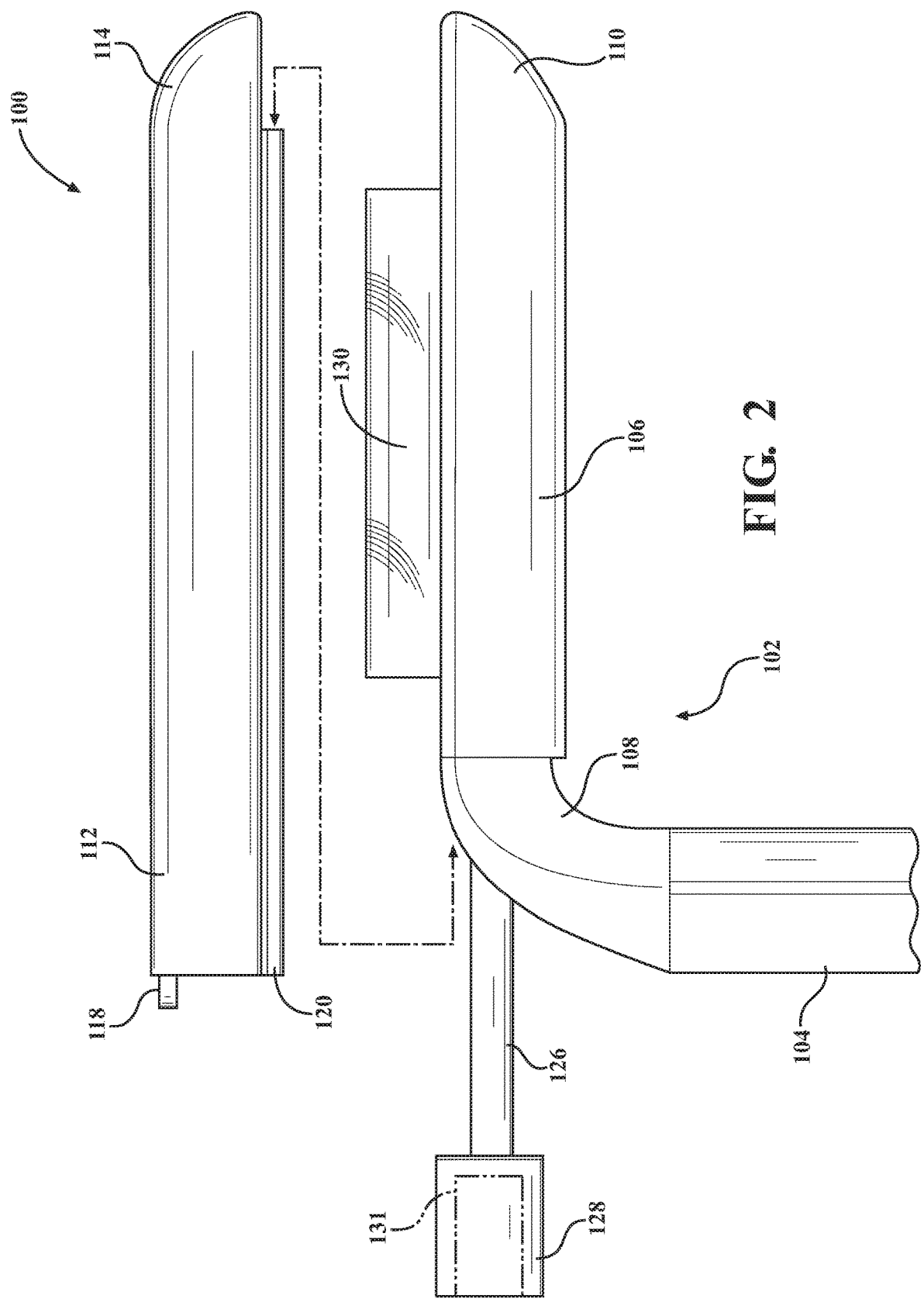
FIG. 2 is an exploded side elevational view of the vaginal speculum and side wall retractor shown in FIG. 1, with the phantom lines showing that an upper blade is selectively slid into a lower blade.

With reference to FIGS. 1 and 2, the main body 102 may have a handle 104 and a lower blade 106. The handle 104 may be integrally formed with the lower blade 106. For example, the handle 104 may be connected to the lower blade 106 via a rounded elbow 108. In particular, the handle 104 may be oriented at about a 90° angle relative to the lower blade 106. The handle 104 may have a width that is substantially equal to a width of the lower blade 106. Other suitable angles for the lower blade 106 relative to the handle 104, as well as other suitable dimensions for the handle 104 and the lower blade 106, may also be selected by one skilled in the art.

As shown in FIG. 1, the handle 104 may be hollow. For example, the handle 104 may have a cross-section that is substantially D-shaped. Advantageously, the hollow handle 104 allows the speculum 100 to be lightweight. Further, the handle 104 allows blood and other bodily material to flow through the speculum 100, in operation.

Referring to FIGS. 11-12, the lower blade 106 may have a substantially U-shaped cross-section. The lower blade 106 may have a length and width that are suitable for insertion and use in a human vagina.

With renewed reference to FIGS. 1 and 2, the lower blade 106 has a free end 110. The free end 110 may be rounded and tapered in shape. In particular, and due to the U-shaped cross-section of the lower blade 106, the end 110 may be spoon-shaped. Advantageously, the shape of the end 110 of the lower blade 106 allows a cervix to be supported atraumatically in operation. However, it should be understood that one skilled in the art may select any other suitable shape for the end 110 of the lower blade 106, as desired.

In certain embodiments, the speculum 100 may have an upper blade 112 to facilitate an introduction of the speculum 100 into a patient. The upper blade 112 is configured for horizontal displacement from the lower blade 106. The upper blade 112 may have a shape that is substantially symmetrical to a shape of the lower blade 106. For example, the upper blade 112 may have a substantially U-shaped cross-section. The upper blade 112 may also have an end 114 that is rounded and tapered in shape, and which also may be substantially spoon-shaped. Other suitable shape and dimensions for the upper blade 112 may also be selected by a skilled artisan within the scope of the present disclosure.

The upper blade 112 may have an other or free end 116. The free end 116 of the upper blade 112 may have a handle or grip tab 118 formed therewith. The tab 118 permits for a user to grip and move the upper blade 112. Although the tab 118 is shown as a semi-circular bridge attached to the other end 116, one skilled in the art may select any other suitable shape for the tab 118, as desired.

Figure 3:
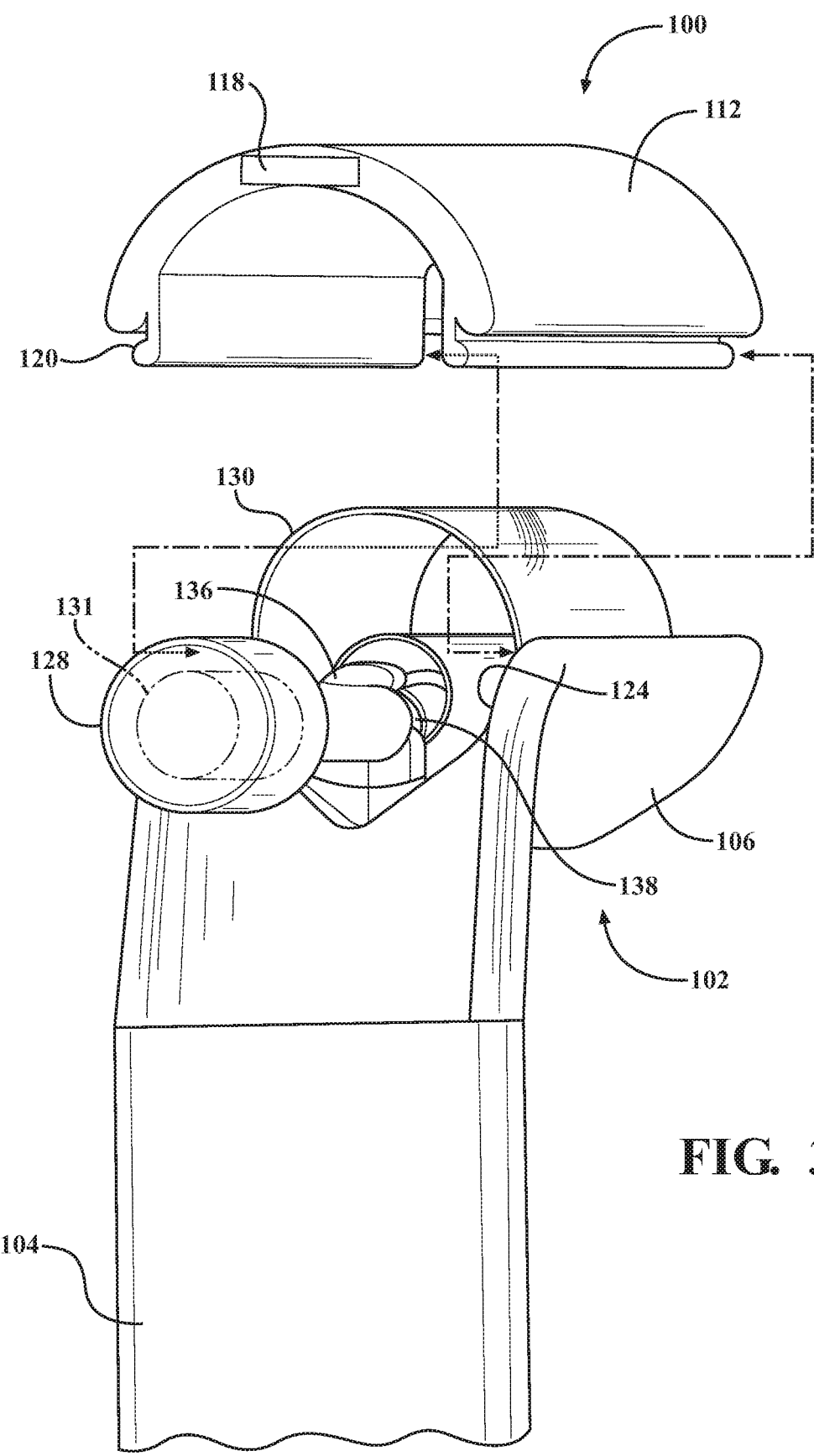
FIG. 3 is an exploded rear perspective view of the vaginal speculum and side wall retractor shown in FIG. 1, with the phantom lines showing that the upper blade is selectively slid into the lower blade.
Figure 4:
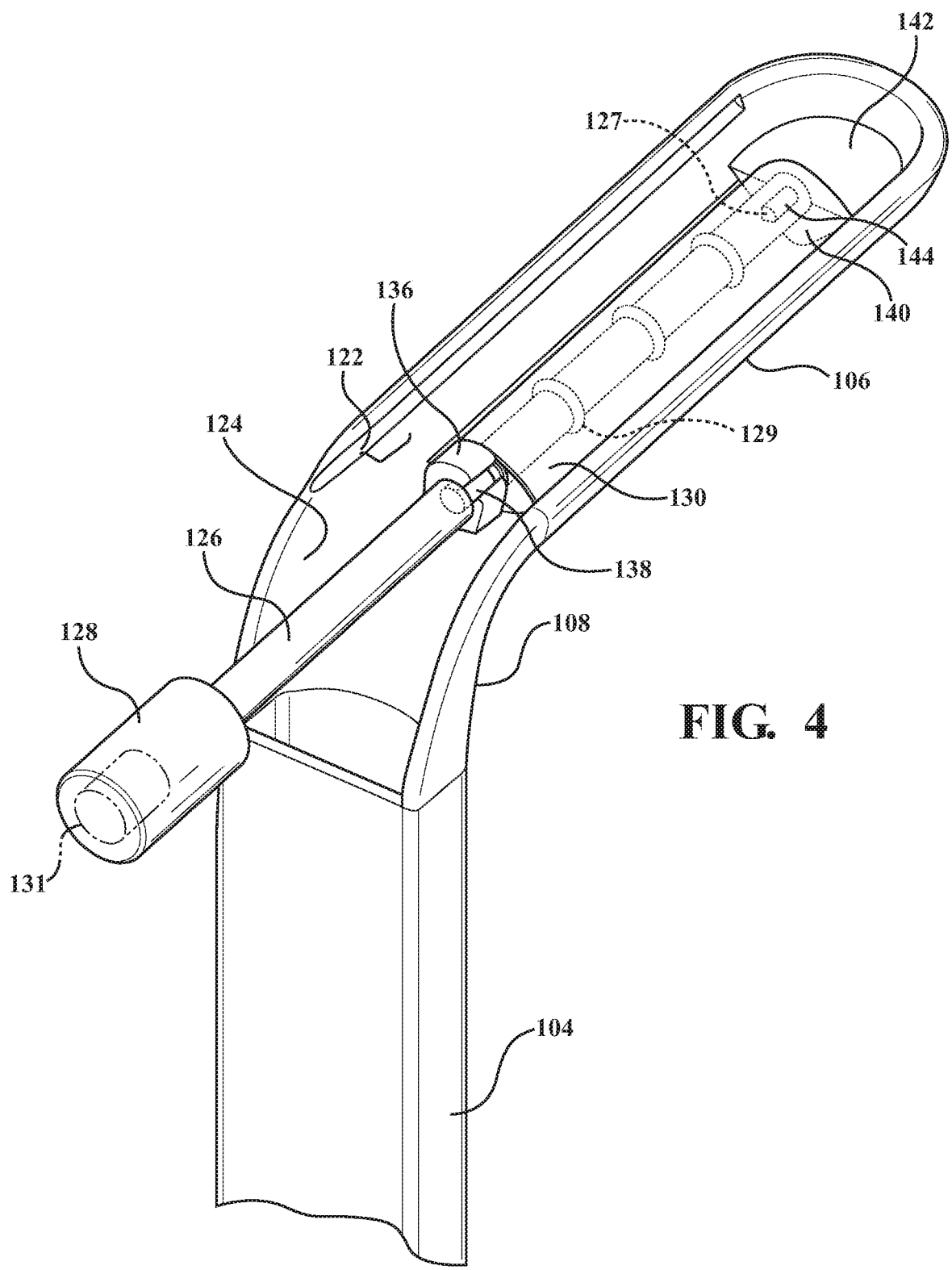
FIG. 4 is a top perspective view of the vaginal speculum and side wall retractor shown in FIG. 1, and with structure disposed within a rolled sheet of the vaginal speculum and side wall retractor depicted by phantom lines.

As shown in FIGS. 3 and 4, the upper blade 112 is removably coupled to the lower blade 106, and in particular, is selectively attached to the lower blade 106 and removable by horizontal displacement or sliding of the upper blade 112 away from the lower blade 106. For example, the upper blade 112 may have a pair of tracks 120. The pair of tracks 120 may depend from an interior surface of the upper blade 112, for example, as shown in FIG. 3. Each of the pair of tracks 120 depend from a primary body of the upper blade 112 at a location adjacent to a side of the upper blade 112.

Referring to FIG. 4, it should be understood that the lower blade 106 may have a pair of channels 122, which correspond generally with the tracks 120. In particular, the channels 122 of the lower blade 106 are configured to receive the pair of tracks 120 from the upper blade 112. The pair of channels 122 of the lower blade 106 are formed in a major interior surface 124 of the lower blade 106.

The respective tracks and channels 120, 122 are depicted as corresponding rounded shapes. However, it should be understood that any other suitable shape may be selected by one skilled in the art so long as the tracks and channels 120, 122 facilitate a retractable connection between the lower blade 106 and the upper blade 112.

The pair of top tracks 120 and the pair of bottom channels 122 allow the lower blade 106 and the upper blade 112 to connect retractably, for example, by a selective sliding of the upper blade 112 away from the lower blade 106 by the user. In operation, the upper blade 112 may initially be connected to the lower blade 106. Advantageously, the upper blade 112 of the speculum 100 may act as an introducer such that the upper blade 112 allows the speculum 100 to be inserted comfortably into the patient. After the speculum 100 is inserted, the upper blade 112 may then be pulled by the user manually by the tab 118. The upper blade 112 may then be slid off the lower blade 106 by the user.

As further depicted in FIG. 4, the speculum 100 has a side wall retractor including a shaft 126, a knob 128, and a rolled sheet 130. The shaft 126 may be elongate, and substantially cylindrical in shape. The shaft 126 may also have a hollow end 127 that is disposed on the shaft 126 opposite an end to which the knob 128 is attached. In particular, the shaft 126 is rotatable disposed in the main body 102, and the end of the shaft 126 having the knob 128 may protrude outwardly from the main body 102 past the handle 104.

The shaft 126 may have a plurality of friction wheels 129, as further depicted in FIG. 4. The plurality of friction wheels 129 may be rubberized discs or O-rings, for example, which are affixed to the shaft 126 through either friction force or by other suitable means such as adhesive. In certain examples, the friction wheels 129 may be disposed in annular grooves formed in a spaced apart fashion along the length of the shaft 126. In other examples, the plurality of friction 129 wheels may be integrally formed on the exterior of the shaft 126. In all examples, the friction wheels 129 are configured to interact with the rolled sheet 130, which is disposed around the shaft 126, as described further herein.

According to a separate embodiment, the plurality of friction wheels 129 may be gears such as sprocket gears (not shown). In this embodiment, the teeth of the gears are configured to interact with the rolled sheet 130 via a plurality of corresponding openings regularly spaced apart in the rolled sheet 130. Each of the openings may be configured to receive a single one of the teeth from one of the gears. Other suitable means for permitting the shaft 126 to interact with the rolled sheet 130 may also be employed, as desired.

As disclosed hereinabove, the knob 128 is disposed on the other end of the shaft 126 opposite the hollow end 127. The knob 128 may be substantially cylindrical in shape, for example. In particular examples, the knob may be provided with knurls or a rubberized coating that facilitates a gripping of the knob 128 by the user. The knob 128 may have a diameter that is larger than a diameter of the shaft 126. The knob 128 may also house a light 131, such a LED light and a battery (not shown). The light 131 may be capable of producing both white and green light. Advantageously, in operation, the light 131 may illuminate the shaft 126, which may be formed from a transparent material suitable to conduct the lighting along the length of the shaft 126, which may in turn illuminate the vaginal cavity.

In an alternative embodiment, the speculum 100 may be provided with a motor and power source instead of a knob, which together permit for an operation of the shaft 126 in an automated manner, for example, by pressing a button in communication with the motor to either furl or unfurl the rolled sheet 130.

The rolled sheet 130 of the speculum 100 is fabricated from a material that has sufficient strength to retract vaginal walls. The rolled sheet 130 of the speculum 100 may be made from a flexible thermoplastic material such as nylon, as a non-limiting example. The edges of the rolled sheet 130 may also be rubberized. The rolled sheet 130 may also be transparent, so as to permit the illumination of the vaginal cavity. In addition to permitting for retraction and supporting of vaginal walls when unfurled, the rolled sheet 130 is also pliable so as to be rolled into the main body 102 where not in operation.

In particular, the rolled sheet 130 has a primary body with a first edge 132 and a second edge 134. The first edge 132 is either affixed to or coiled around the shaft 126, and the primary body of the rolled sheet 130 is generally coiled around the shaft 126. The second edge 134 is affixed to the major interior surface 124 of the lower blade 106, as shown in FIG. 5.

With renewed reference to FIGS. 3 and 4, the major interior surface 124 of the lower blade 106 may have a clip 136. The clip 136 is disposed on and attached to the major interior surface 124 adjacent to rounded elbow 108. The clip 136 is configured to receive the shaft 126 and permit for a selective rotation of the shaft 126 by a turning of the knob 128 by the user. The clip 136 may be substantially C-shaped, for example. Other suitable shapes for the clip 136 may also be employed, as desired.

In particular, the clip 136 may have a connection recess 138. The connection recess 138 is defined by the clip 136, and may have a diameter that is equal to or smaller than the diameter of the shaft 126. The shaft 126 may also be provided with an area of decreased diameter that allows it to mate with the clip 136. This relative sizing of the connection recess 138 allows the clip 136 to securely hold the shaft 126 at the connection recess 138. Advantageously, the clip 136 holds the shaft 126 in place and militates against undesirable lateral movement of the shaft 126. The sizing of the connection recess 138 of the clip 136 also permits the shaft 126 to rotate by the user turning the knob 128, in order to open the speculum 100, while militating against an undesirable counter-rotation of the shaft 126 due to the force of the rolled sheet 130 alone when unfurled.

Figure 5:
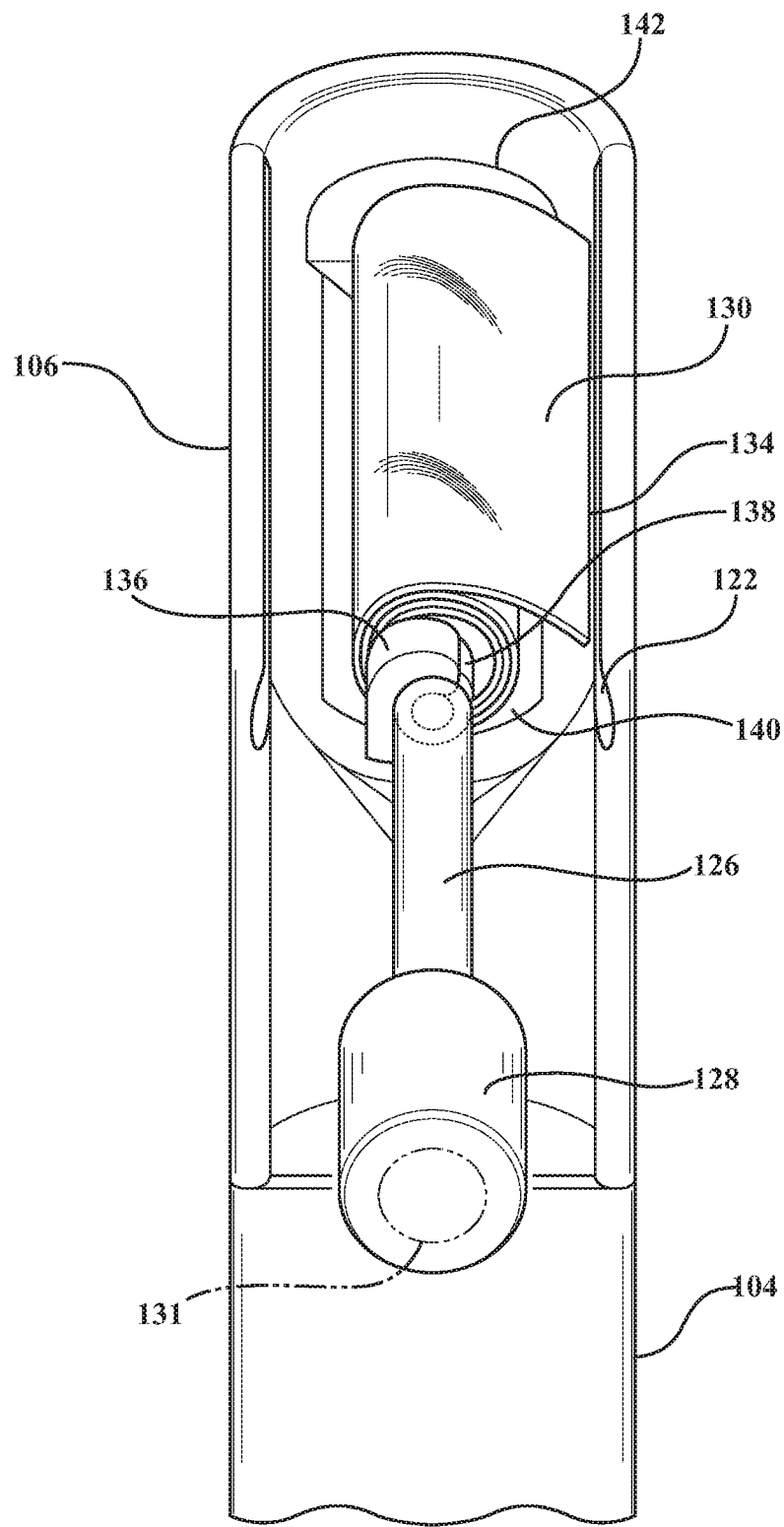
FIG. 5 is a top perspective view of the vaginal speculum and side wall retractor as shown in FIG. 1.

With reference to FIG. 5, the major interior surface 124 may further have a recessed groove 140 formed therein. The recessed groove 140 may extend across a length of the major interior surface 124 beneath the shaft 126. In particular, the recessed groove 140 may extend from the clip 136 to a traverse wall 142 formed in the lower blade 106. Advantageously, the recessed groove 140 may receive and house the rolled sheet 130 prior to it being unfurled in operation.

The recessed groove 140 may also allow the shaft 126 and the rolled sheet 130 to be recessed more deeply within the lower blade 106. Advantageously, this deeper positioning of the rolled sheet 130 and the shaft 126 may allow the operator of the speculum 100 greater visibility of the vaginal cavity during use of the speculum 100.

As shown in FIG. 4, the traverse wall 142 may be formed on the major interior surface 124 of the lower blade 106. The traverse wall 142 may span an entire width of the lower blade 106, for example. The traverse wall 142 may also have a height that is less than a maximum height of the lower blade 106, so that an uppermost portion of the traverse wall 142 is spaced apart from an uppermost lip or edge of the lower blade 106.

In particular embodiments, as illustrated in FIG. 4, the traverse wall 142 may have a pin 144 extending outwardly therefrom toward the hollow end 127 of the shaft 126. The pin 144 is spaced apart from a surface of the recessed groove 140, and loosely disposed in the hollow end 127 of the shaft 126. In this manner, the pin 144 likewise supports the shaft 126 above the surface of the recessed groove 140, and permits for a rotational movement of the shaft 126 by the user turning the knob 128 that is fixedly attached to the other end of the shaft 126.

It should be appreciated that the pin 144 allows for the shaft 126 to freely rotate by the turning of the knob 128. The clip 136 and the pin 144 also militate against undesirable lateral movement of the shaft 126, while allowing desirable rotation of the shaft 126. Other suitable means for supporting the shaft 126 while permitting the rotational movement may also be employed, as desired.

In certain embodiments, not shown, the shaft 126 may also be removed following insertion of the main body. This advantageously allows separate instruments to be inserted in the vaginal cavity.

In operation, the vaginal speculum and side wall retractor 100, may be introduced to the vaginal cavity of a patient by the user or operator such as a physician for a procedure, where the rolled sheet 130 is in a furled state. The upper blade 112 may then be displaced horizontally by the user pulling the tab 118. In turn, this causes the upper blade 112 to slide off of the lower blade 106.

Once the upper blade 112 is displaced and removed from the lower blade 106, the rolled sheet 130 may be unfurled or unrolled by the operator by twisting the knob 128, 128'. The knob 128 causes the shaft 126 to rotate within the clip 136 and about the pin 144. The rotating shaft 126 in turn causes friction between the rolled sheet 130 and the friction wheels 128.

Due to the rotating of the knob 128, the rolled sheet 130 may then unfurl and begin to exact pressure on the side walls of the vaginal cavity, as shown in FIG. 12. Advantageously, the rolled sheet 130 is able to apply a substantially even pressure to all adjacent vaginal wall surfaces simultaneously. Optionally, and as discussed hereinabove, the shaft 126 may be removed to allow the operator to insert additional instruments into the vaginal cavity for the procedure.

In order to remove the speculum 100 following the procedure, the rolled sheet 130 may be refurled or rewound. With the shaft 126 in place on the speculum 100, the knob 128 may be turned in a direction opposite it was turned to originally unfurl the sheet 130. In this manner, the knob 128 causes the shaft 126 to rotate within the clip 136 and about the pin 144.

The rotating shaft 126 may cause friction between the rolled sheet 130 and the friction wheels 128. The rolled sheet 130 may then be refurled or rewound up, which likewise removes the pressure on the side walls of the vaginal cavity. In certain embodiments, the rolled sheet 130 must be fully refurled or rewound before the speculum 100 is removed from the patient.

In FIGS. 6-10, the vaginal speculum 100' according to another embodiment of the disclosure is shown. Like or related structure to that shown in FIGS. 1-5 is identified in FIGS. 6-10 with a same reference number and a prime (') symbol for purpose of clarity.

As shown in FIGS. 6-10, the speculum 100' may further include an opening mechanism 146' for vertical displacement of the upper blade 112' from the lower blade 106' instead of the horizontal displacement described with respect to FIGS. 5-9. The opening mechanism 146' may control a vertical displacement between the upper blade 112' and the lower blade 106'. The opening mechanism 146' may also couple the upper blade 112' and the handle 104', for example.

Figure 8:
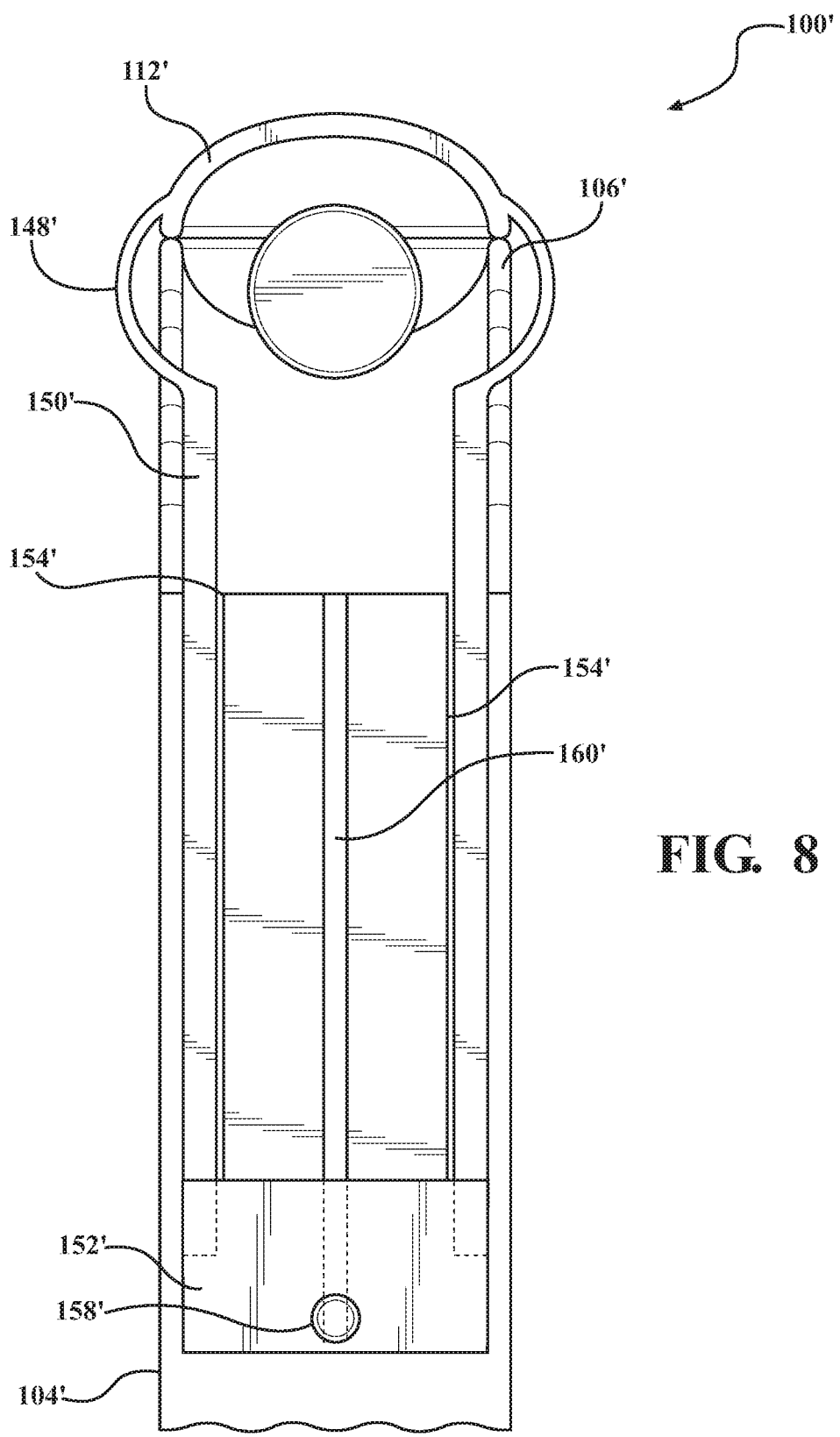
FIG. 8 is a rear elevational view of the vaginal speculum and side wall retractor of FIG. 6, shown in a closed position.
Figure 9:
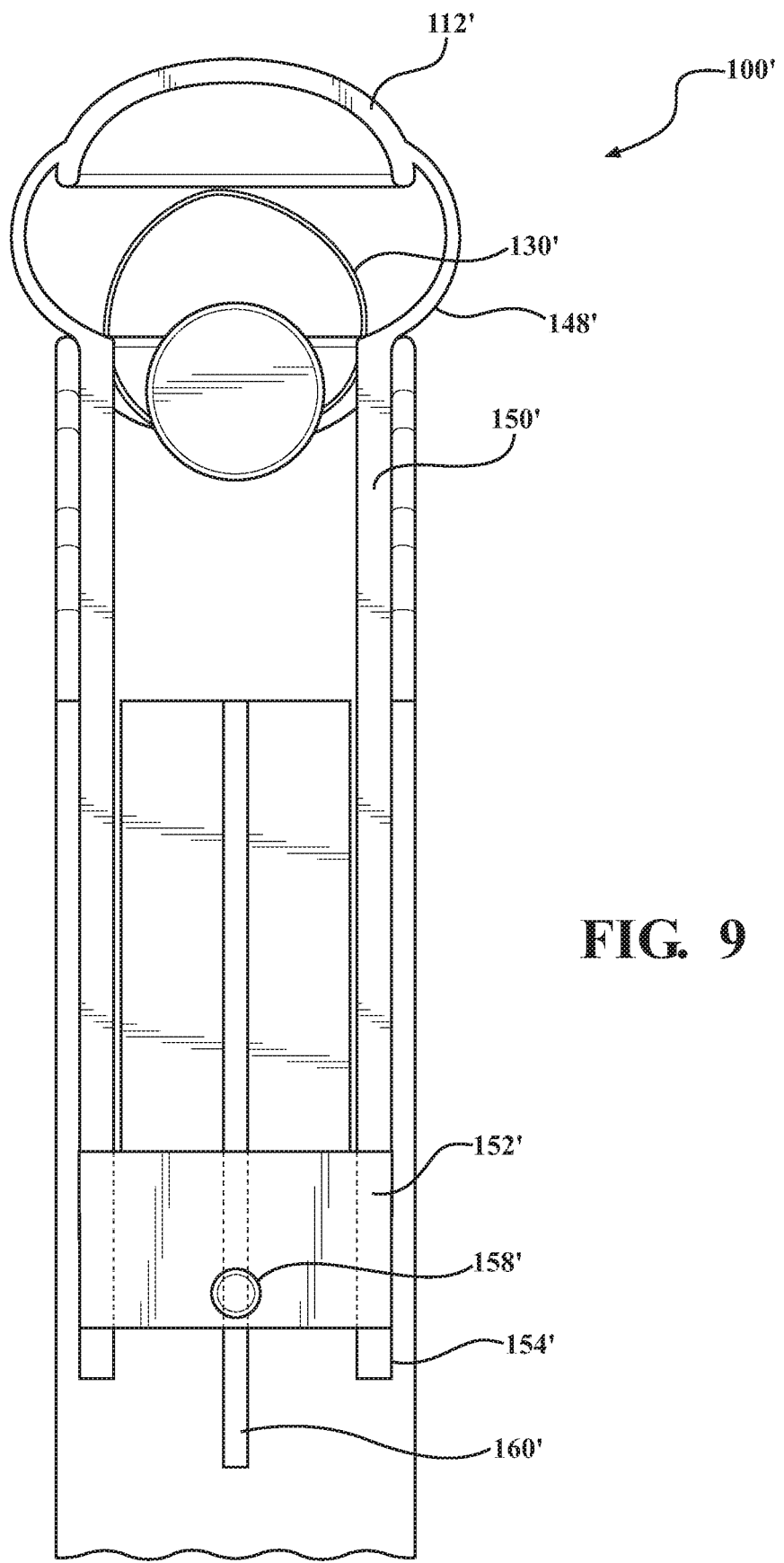
FIG. 9 is a rear elevational view of the vaginal speculum and side wall retractor of FIG. 6, shown in a partially open position.

In particular embodiments, the opening mechanism 146' may have a pair of curved portions 148', a pair of straight portions 150', and a grip or tab 152'. Each of the pair of straight portions 150' is disposed on opposite sides of the tab 152'. Each of the pair of curved portions 148' may be disposed on and attached to one of the pair of straight portions 150'. Each of the curved portions may be disposed on opposite sides of an exterior of the upper blade 112', for example, as shown in FIGS. 8 and 9. Each of the pair of curved portions 148', the pair of straight portions 150', and the tab 152' may be integrally formed as a single unit, or formed as separate units and subsequently assembled, as desired.

As shown in FIG. 8-10, each of the pair of curved portions 148' may have a substantially C-shaped cross-section. Likewise, the pair of curved portions 148' may extend outwardly such that the pair of curved portions 148' extend over either side of the handle 104'. Advantageously, this particular shape of the pair of curved portions 148' may provide for a relative increase in lateral room for a procedure compared to a speculum 100' without curved portions 148', in operation.

With continued reference to FIGS. 8-10, the handle 104' may have a pair of channels 154' formed therein. The pair of channels 154' may correspond with the pair of straight portions 150' of the opening mechanism 146'. Accordingly, each of the pair of straight portions 150' may be disposed in one of the pair of channels 154' in the handle 104'. It should be appreciated that each of the pair of straight portions 150' may have an L-shaped cross-section, which permits for the slidable but secure positioning of the straight portions 150' within the channels 154', as desired.

The tab 152' may be disposed in the handle 104'. The tab 152' may be substantially rectangular in shape, for example, although other suitable shapes may also be used. In particular, the tab 152' may have a width that is substantially equal to a width of the handle 104'. Each of the straight portions 150' are disposed on the tab 152'. The tab 152' may slide in the channels 154' of the handle 104', thereby allowing for the selective raising and lowering of the straight portions 150' of the opening mechanism 146', and likewise the raising and lower of the upper blade 112', by the manual movement of the tab 152' by the user as shown in FIGS. 8-10.

In particular embodiments, the tab 152' may have an aperture 156' formed therethrough. The aperture 156' may be formed in a center area of the tab 152' and configured to receive a fastener 158' such as a friction lock screw, as a non-limiting example. The fastener 158' may also be disposed in a central elongate slot 160' formed in the handle 104'. Advantageously, the fastener 158' may be tightened to militate against undesirable movement of the opening mechanism 146' in operation. Where the fastener 158' is tightened, thereby locking the opening mechanism 146' into a user-defined position, the speculum 100' may be used without the user or operator manually holding the speculum 100' open for the procedure.

In operation, the vaginal speculum and side wall retractor 100' may be introduced to the vaginal cavity of the patient by the user or operator such as the physician. The upper blade 112' may then be displaced vertically, for example, by raising the tab 152' in the handle 104' until the upper blade 112' reaches the desired vertical displacement. There the fastener 158' may then be tightened in order to hold the upper blade 112' at the desired vertical displacement.

Once the upper blade 112' is sufficiently displaced, the rolled sheet 130' may be unfurled or unrolled by the operator by twisting the knob 128'. The knob 128' may cause the shaft 126' to rotate within the clip 136' and about the pin 144'. The rotating of the shaft 126' may cause friction between the rolled sheet 130' and the friction wheels 128'.

The rolled sheet 130' may then unfurl and begin to exact pressure on the side walls of the vaginal cavity of the patient, in a manner similar to that shown in FIG. 12. Advantageously, the rolled sheet 130' is able to apply substantially even pressure to all adjacent vaginal wall surfaces simultaneously.

In order to remove the speculum 100', the rolled sheet 130' may be refurled or rewound. With the shaft 126' in place on the speculum 100', the knob 128' may be turned in the opposite direction that is was turned to originally unfurl or unwind the rolled sheet 130'. The knob 128' may cause the shaft 126' to rotate within the clip 136' and about the pin 144'.

The rotating of the shaft 126' may cause friction between the rolled sheet 130' and the friction wheels 128'. The rolled sheet 130' may then be refurled or wound up and begin to remove pressure on the side walls of the vaginal cavity. In certain embodiments, the rolled sheet 130' may be fully wound up before the speculum 100' is removed from the patient.

It should be understood that the vaginal speculum and side wall retractor 100, 100' of the present disclosure allows clinicians to have an unobstructed view of the cervix and vaginal walls. The speculum 100, 100' militates against the vaginal side walls collapsing into the clinician's field of view.

While certain representative embodiments and details have been shown for purposes of illustrating the invention, it will be apparent to those skilled in the art that various changes may be made without departing from the scope of the disclosure, which is further described in the following appended claims.

What is claimed is:

1. A vaginal speculum, comprising,
a main body including a handle coupled to a lower blade;
an upper blade removably coupled to the lower blade and configured for one of horizontal displacement and vertical displacement relative to the lower blade; and
a side wall retractor disposed on the lower blade, the side wall retractor having a shaft and a rolled sheet, wherein the shaft is configured to unroll the rolled sheet upon rotation of the shaft,
wherein a clip is disposed in the lower blade, the clip supporting and rotatably receiving the shaft above the lower blade.

2. The vaginal speculum of claim 1, wherein the shaft has a hollow end and the lower blade has a pin formed thereon, the hollow end of the shaft receiving and being supported by the pin above the lower blade and permitting for rotation of the shaft.

3. The vaginal speculum of claim 1, wherein the shaft has a plurality of wheels disposed on an exterior thereof, the wheels configured to contact and unroll the rolled sheet upon rotation of the shaft.

4. The vaginal speculum of claim 1, further comprising a knob attached to the shaft, wherein the knob houses a light that illuminates the shaft.

5. The vaginal speculum of claim 1, wherein the lower blade has a substantially U-shaped cross-section.

6. The vaginal speculum of claim 1, wherein the handle is hollow.

7. The vaginal speculum of claim 1, wherein the upper blade is slidably received by the lower blade, and the upper blade is configured for the horizontal displacement relative to the lower blade.

8. The vaginal speculum of claim 7, wherein the upper blade has a pair of tracks and the lower blade has a pair of corresponding channels for slidably receiving the pair of tracks.

9. The vaginal speculum of claim 8, wherein the upper blade has a free end with a grip tab that permits for a user to manually pull the upper blade for the horizontal displacement.

10. The vaginal speculum of claim 9, wherein the grip tab is a semi-circular bridge attached to the free end of the upper blade.

11. The vaginal speculum of claim 1, wherein the upper blade is configured for the vertical displacement relative to the lower blade.

12. The vaginal speculum of claim 11, further comprising an opening mechanism disposed in the handle configured to cause the vertical displacement of the upper blade.

13. The vaginal speculum of claim 12, wherein the opening mechanism includes a pair of supports, a grip tab, and a fastener.

14. The vaginal speculum of claim 13, wherein the pair of supports connect the upper blade and the grip tab.

15. The vaginal speculum of claim 14, wherein the handle has a pair of channels formed therein, and the grip tab is slidably connected to the handle via the channels.

16. The vaginal speculum of claim 15, wherein the grip tab has an aperture formed therethrough, and the handle has a central elongate slot disposed between the pair of channels.

17. The vaginal speculum of claim 16, wherein the fastener is disposed through the aperture of the grip tab and the central elongate slot of the handle, and the fastener is configured to selectively affix the grip tab at a user-defined position along the handle.

18. A vaginal speculum, comprising,
a main body including a handle coupled to a lower blade;
an upper blade removably coupled to the lower blade and configured for horizontal displacement relative to the lower blade; and
a side wall retractor disposed on the lower blade, the side wall retractor having a shaft, a knob, and a rolled sheet, wherein the shaft is configured to unroll the rolled sheet upon rotation of the shaft by the knob,
wherein the upper blade is slidably received by the lower blade, and the upper blade has a pair of tracks and the lower blade has a pair of corresponding channels for slidably receiving the pair of tracks, and the upper blade has a free end with a grip tab that permits for a user to manually pull the upper blade for the horizontal displacement, and the grip tab is a semi-circular bridge attached to the free end of the upper blade, wherein a clip is disposed in the lower blade, the clip supporting and rotatably receiving the shaft above the lower blade.

19. A vaginal speculum, comprising, a main body including a handle coupled to a lower blade;

an upper blade removably coupled to the lower blade, and configured for vertical displacement relative to the lower blade;

a side wall retractor disposed on the lower blade, the side wall retractor having a shaft and a rolled sheet, wherein the shaft is configured to unroll the rolled sheet upon rotation of the shaft; and an opening mechanism disposed in the handle configured to cause the vertical displacement of the upper blade, wherein the opening mechanism includes a pair of supports, a grip tab, and a fastener, the pair of supports connect the upper blade and the grip tab, the handle has a pair of channels formed therein, and the grip tab is slidably connected to the handle via the channels, the grip tab has an aperture formed therethrough, and the handle has a central elongate slot disposed between the pair of channels, and the fastener is disposed through the aperture of the grip tab and the central elongate slot of the handle, and the fastener is configured to selectively affix the grip tab at a user-defined position along the handle, wherein a clip is disposed in the lower blade, the clip supporting and rotatably receiving the shaft above the lower blade.

\* \* \* \* \*